(12) United States Patent
Rapoport et al.

(10) Patent No.: US 8,673,984 B2
(45) Date of Patent: Mar. 18, 2014

(54) STABLE PERFLUOROCARBON EMULSION FOR USE AS AN ARTIFICIAL OXYGEN CARRIER

(75) Inventors: Natalya Y. Rapoport, Sandy, UT (US); Glenn D. Prestwich, Eastsound, WA (US); Russell Morris Condie, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/133,126

(22) PCT Filed: Dec. 8, 2009

(86) PCT No.: PCT/US2009/067179
§ 371 (c)(1),
(2), (4) Date: Aug. 22, 2011

(87) PCT Pub. No.: WO2010/077671
PCT Pub. Date: Jul. 8, 2010

(65) Prior Publication Data
US 2011/0306581 A1    Dec. 15, 2011

Related U.S. Application Data

(60) Provisional application No. 61/201,261, filed on Dec. 8, 2008.

(51) Int. Cl.
*A61K 31/025* (2006.01)

(52) U.S. Cl.
USPC ............................................ 514/756; 514/832

(58) Field of Classification Search
USPC .................................................. 514/756, 832
See application file for complete search history.

(56) References Cited

U.S. PATENT DOCUMENTS

| | | | |
|---|---|---|---|
| 2,674,619 A * | 4/1954 | Lundsted | 560/198 |
| 4,105,798 A | 8/1978 | Moore et al. | |
| 4,395,393 A | 7/1983 | Schmolka | |
| 5,077,036 A | 12/1991 | Long, Jr. | |
| 5,434,191 A | 7/1995 | Dandliker et al. | |
| 5,595,687 A | 1/1997 | Raynolds et al. | |
| 5,904,933 A | 5/1999 | Riess et al. | |
| 2004/0068020 A1 | 4/2004 | Weers et al. | |
| 2007/0026024 A1 | 2/2007 | Drees | |

FOREIGN PATENT DOCUMENTS

| | | |
|---|---|---|
| EP | 0091820 | 10/1983 |
| JP | 60255718 | 12/1985 |
| JP | 61233615 | 10/1986 |
| WO | WO 2007/014328 | 2/2007 |

OTHER PUBLICATIONS

Gao et al.; Drug-Loaded Nano/Microbubbles for Combing Ultrasonography and Targeted Chemotherapy; Ultrasonics; 2007; 11 pages.
Rapoport; Multifunctional Nanoparticles for Combing Ultrasonic Tumor Imaging and Targeted Chemotherapy; JNCI; Jul. 18, 2007; pp. 1065-1106; vol. 99, issue 14.
Spahn; Blood Substitutes, Artificial Oxygen Carriers: Perfluorocarbon Emulsions; Crit Care; Sep. 24, 1999; pp. R93-R97; vol. 3, No. 5.
Spiess et al.; Perfluorocarbon Emulsions and Cardiopulmonary Bypass: A Technique for the Future; Journal of Cardiothoracic and Cascular Anesthesia; Jan. 1996; pp. 83-90; vol. 10, No. 1.
Standl; Artificial Oxygen Carriers as Red Blood Cell Substitutes—Perfluorocarbons and Cell-Free Hemoglobin; Infus Ther Med; 2000; pp. 128-137; vol. 27.
Condie et al.; Development of a Stable Artificial Oxygen Carrier for Tissue Engineering; poster; 1 page; 4th Annual Mountain West Biomedical Engineering Conference; Salt Lake City, Utah; Sep. 5, 2008.
Condie et al.; Development of a Stable Artificial Oxygen Carrier for Tissue Engineering; abstract; 1 page; 4th Annual Mountain West Biomedical Engineering Conference; Salt Lake City, Utah; Sep. 5, 2008.

* cited by examiner

*Primary Examiner* — Kevin E Weddington
(74) *Attorney, Agent, or Firm* — Thorpe North & Western LLP

(57) ABSTRACT

Perfluorocarbon emulsions having a high stability and good oxygen release are disclosed and described. These perfluorocarbon emulsions are typically for use as artificial oxygen carriers. The perfluorocarbon emulsions include a disperse phase of a perfluorocarbon and an emulsion stabilizer, and continuous phase. The emulsion stabilizer can primarily include a poly(ethylene oxide) block copolymer. These stabilized perfluorocarbon emulsions can be used in liquid and/or hydrogel phases of perfusion bioreactors or various other culture systems to enhance cell viability in thick tissue constructs, or as blood substitutes, although other applications may also be considered.

27 Claims, 3 Drawing Sheets

STABLE PERFLUOROCARBON EMULSION FOR USE AS AN ARTIFICIAL OXYGEN CARRIER

RELATED APPLICATIONS

This application is a national stage entry of International Application No. PCT/US09/67179, filed Dec. 8, 2009, which claims benefit of U.S. Provisional Application No. 61/201,261, filed on Dec. 8, 2008, and which are each incorporated by reference herein.

GOVERNMENT INTEREST

This invention was made with government support under Grant No. R01 EB1033 awarded by the National Institutes of Health and Graduate Research Fellowship No. 2007051771 awarded by the National Science Foundation. The United States government has certain rights in this invention.

FIELD OF THE INVENTION

This invention relates to perfluorocarbon emulsions as synthetic oxygen carriers. Therefore, the present invention relates generally to the fields of emulsion chemistry and biomedical engineering.

BACKGROUND OF THE INVENTION

A wide variety of artificial oxygen carriers have been developed over the past century. Many of these are based on perfluorocarbon emulsions, some of which have been used since World War II. Despite moderate success for particular applications, current emulsions exhibit a number of weaknesses which can limit their effectiveness and potential applications. Some of these limitations include limited stability, unacceptable toxicity, undesirable host reactions, and non-optimal oxygen release characteristics. For example, most current commercial perfluorocarbon emulsions have a half-life in vivo of less than an hour, and often less than fifteen minutes. Thus, stability remains one of the primary deficiencies of current perfluorocarbon emulsion compositions. Current surfactant-stabilized dispersion droplets tend to coalesce via Ostwald ripening ultimately leading to breakdown of the emulsions.

A promising new application of artificial oxygen carriers is maintaining tissue oxygen levels in bioreactors, a little-explored topic with profound implications for improving the relevance of in vitro models. Moreover, the challenge of exchanging oxygen, nutrients, and wastes typically limits the thickness of engineered tissues to a few hundred micrometers. Therefore, improved artificial oxygen carriers and methods of using such carriers continue to be sought.

SUMMARY

In light of the problems and deficiencies noted above, perfluorocarbon emulsions which have reduced limitations and substantially improved stability are disclosed and described. A stable artificial oxygen carrier (AOC) can include a stabilized perfluorocarbon emulsion for use in liquid and/or hydrogel phases of perfusion bioreactors and other culture systems. The perfluorocarbon emulsions can effectively carry oxygen and are highly stable at temperatures ranging from 4° C. to at least about 37° C., including room temperature. They can also be effectively used to enhance cell viability in thick tissue constructs or as blood substitutes, although other applications may also be considered.

These perfluorocarbon emulsions can be used as artificial oxygen carriers. More particularly, the emulsions can include a disperse phase of a perfluorocarbon, an emulsion stabilizer, and an aqueous continuous phase. The emulsion stabilizer can include primarily a block copolymer composed of poly (ethylene oxide) (PEO) and a more hydrophobic polymer.

This broad outline of the more important features of the invention is intended to improve understanding of the detailed description thereof that follows and of the present contribution to the art. Other features of the present invention will become clear from the detailed description of the invention below, taken with the accompanying figures and claims, or may be learned by the practice of the invention.

BRIEF DESCRIPTION OF THE DRAWINGS

The present invention will become more fully apparent from the following description and appended claims, taken in conjunction with the accompanying drawings. These drawings merely depict exemplary embodiments of the present invention and therefore they are not to be considered limiting of its scope. It will be readily appreciated that the components of the present invention, as generally described and illustrated in the figures herein, could be arranged, sized, and designed in a wide variety of different configurations. Nonetheless, the invention will be described and explained with additional specificity and detail through the use of the accompanying drawings in which:

DETAILED DESCRIPTION OF EXEMPLARY EMBODIMENTS

Figure 1:
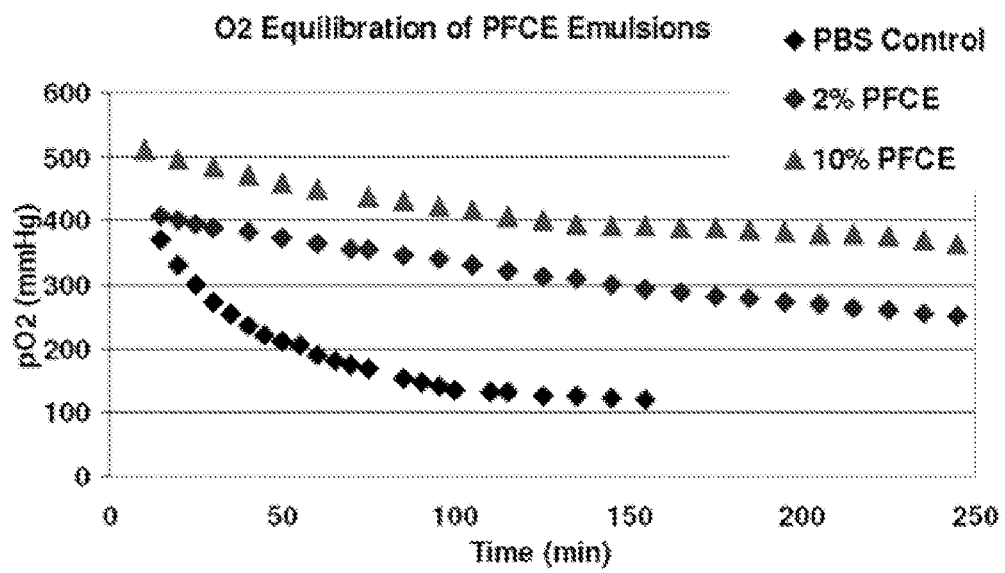
FIG. 1 is a graph showing decline in $pO_2$ of 1 ml oxygen saturated perfluorocarbon emulsions exposed to ambient air after $O_2$ bubbling was discontinued.

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

DEFINITIONS

In describing and claiming the present invention, the following terminology will be used.

The singular forms "a," "an," and "the" include plural referents unless the context clearly dictates otherwise. Thus, for example, reference to "a copolymer" includes reference to one or more of such materials and reference to "sonicating" or "exposing" refers to one or more such steps.

As used herein, "artificial oxygen carrier" refers to a synthetic composition which is capable of absorbing oxygen, adsorbing oxygen and/or stabilizing dissolved oxygen in solution, and then releasing the oxygen over an extended delivery time. Such artificial oxygen carriers can be used in preparing artificial blood, support artificial tissue growth or other use in physiological systems, although other non-biological applications could also be served by such oxygen carriers.

As used herein, "biodegradable" refers to an ability of a substance to be broken down into simpler molecules by enzymatic or other biological action in the environment to which the substance is exposed. Biodegradation can involve complete mineralization, although this is not required. In the context of the present invention, biodegradability also indicates that biodegradation products are substantially less toxic or harmful than the original substance.

As used herein, when referring to a component of a composition, "primarily" indicates that that component is present in a greater amount than any other component of the relevant composition. For example, an emulsion stabilizer composition, within the emulsion, which stabilizer is primarily an ethylene oxide copolymer may have multiple surfactants, and or additives as part of the stabilizer composition. However, the copolymer will be present in an amount which is more than any other single component of the stabilizer.

As used herein, "tissue construct" refers to any ex vivo cultured collection of cells (including matrix components, any signaling factors and other active components or additives) to form a three-dimensional structure. Such tissue constructs can involve use of specialized scaffolding, controlled stress or flow environments, or other conditions to enhance growth of a desired tissue.

As used herein with respect to an identified property or circumstance, "substantially" refers to a degree of deviation that is sufficiently large so as to measurably detract from the identified property or circumstance. The exact degree of deviation allowable may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims unless clearly indicated otherwise. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Perfluorocarbon Emulsions

Perfluorocarbon emulsions for use as artificial oxygen carriers can have extended stability and oxygen carrying capacity. More particularly, the perfluorocarbon emulsions include a disperse phase of a perfluorocarbon and an emulsion stabilizer, and a continuous phase. The emulsion stabilizer can include multiple components, but is typically primarily a poly(ethylene oxide) (PEO) block copolymer. In some embodiments, the poly(ethylene oxide) block copolymer can comprise a majority of the emulsion stabilizer. Currently, one specific embodiment includes an emulsion stabilizer which consists essentially of the poly(ethylene oxide) block copolymer.

The emulsion stabilizer includes the poly(ethylene oxide) block copolymer, although other secondary surfactants and/or additives can optionally be present. In one specific embodiment, the poly(ethylene oxide) block copolymer is a poly(ethylene oxide)-polyester block copolymer. Non-limiting examples of suitable poly(ethylene oxide)-polyester block copolymers include poly(ethylene oxide) block copolymers with ε-caprolactone, (L or D,L) lactide, D,L-lactic acid, D-lactic acid, L-lactic acid, glycolide, glycolic acid, lactic and glycolic acid (PLGA), hydroxy hexanoic acid, γ-butyrolactone, γ-hydroxy butyric acid, δ-valerolactone, hydroxy valeric acid, hydroxybutyric acids, malic acid, copolymers thereof, and combinations thereof. Poly(ethylene oxide)-block-poly ε-caprolactone copolymer exhibits a particularly effective combination of stability, rigidity in mechanical strength of micelle walls, and high elasticity. Alternatively, the poly(ethylene oxide) block copolymer can be a poly(ethylene oxide)-polyether block copolymer. Non-limiting examples of suitable poly(ethylene oxide)-polyether block copolymers include a polyethylene-polyether triblock copolymer such as Pluronics.

In some embodiments, it can be desirable that the composition be substantially free of phospholipids which have a significantly lower stability than the above block copolymers. Although stability is desirable, once the oxygen is delivered, excessive stability can render the compositions or compounds toxic or otherwise problematic. As such, the poly(ethylene oxide) block copolymer can also be biodegradable sufficient to prevent long-term accumulation of the same in tissues of a host, e.g. liver etc.

The specific content of the emulsion stabilizer can depend largely on the copolymers and corresponding components chosen (e.g. perfluorocarbon and/or optional additives). However, generally the emulsion stabilizer can be present from about 1 vol % to about 20 vol % of the perfluorocarbon emulsion, and most often from about 5 vol % to about 10 vol %.

As the effective oxygen carrying species, a perfluorocarbon can be incorporated into the emulsion. Perfluorocarbons can greatly extend tissue thickness, especially when incorporated in perfusion bioreactors. Generally, no specific limitation on suitable perfluorocarbons is necessary, depending on the particular application, other than suitable vapor pressure and oxygen binding capacity. Non-limiting examples of suitable perfluorocarbons can include perfluoroalkyl ethers; perfluoro crown ethers such as perfluoro-15-crown-5-ether having a structure

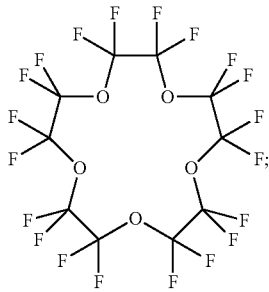

perfluoroalkanes such as perfluoropentane, perfluorohexane, perfluorononane, perfluorohexyl bromide, perfluorooctyl bromide, and perfluorodecyl bromide; perfluoroalkenes such as bisperfluorobutylethylene; perfluorocycloalkanes such as perfluorodecalin, perfluorocyclohexanes, perfluoroadamantane, perfluorobicyclodecane, and perfluoromethyl decahydroquinoline; perfluoro amines such as perfluoroalkyl amines; and C1-C8 substituted compounds thereof, isomers thereof, and combinations thereof.

Depending on the particular application, the volatility, vapor pressure and/or boiling point of the perfluorocarbon can affect performance and suitability. Generally, for mammal in vivo applications, a boiling point greater than about 37° C. such as over about 50° C. can be desirable. Further, increased long-term stability of micelles can often be realized by choosing a perfluorocarbon having a boiling point which is substantially higher, such as greater than about 120° C. For example, perfluoro-15-crown-5-ether has a boiling point of about 140° C. which has shown excellent stability results as illustrated in the examples below. The perfluorocarbon can be present as a single perfluorocarbon compound or a mixture of such compounds. In some cases, a mixture of perfluorocarbon compounds can allow for optimization or customization of boiling temperature and control of droplet to bubble transitions.

As with the emulsion stabilizer, the content of perfluorocarbon in the emulsion can vary depending on the particular species chosen for each component. However, as a general guideline, the perfluorocarbon can be present from about 1 vol % to about 80 vol % of the perfluorocarbon emulsion, although up to 95 vol % may be achieved depending on the perfluorocarbon chosen. In one specific embodiment the perfluorocarbon can be present from about 2 vol % to about 20 vol %. In other embodiments, the perfluorocarbon can be present in higher concentrations such as from about 40 vol % to about 70 vol %. The concentration of perfluorocarbon can vary considerably depending on the particular application and desired oxygen demand. For example, high oxygen demand perfusion reactors can benefit from higher perfluorocarbon concentration. High concentration emulsions can also be diluted in culture media, greatly simplifying formulation.

In another aspect, the ratio of stabilizer to perfluorocarbon can be controlled. Generally, the ratio of stabilizer to perfluorocarbon can be about 0.006:1 to about 2:1, and in some cases can be about 0.025:1 to about 1.6:1, and in other cases from about 0.025:1 to about 0.4:1.

The perfluorocarbon emulsions can typically have relatively small droplet sizes. Although specific droplet sizes can vary, the disperse phase has a droplet size can generally range from about 100 nm to about 800 nm, and most often from about 200 nm to about 500 nm.

Although some embodiments can consist essentially of a single polyethylene oxide copolymer, the perfluorocarbon, and an aqueous vehicle, other additives can be optionally included. Suitable additives for the perfluorocarbon emulsions can include, but are not limited to, hydrogels, antioxidants, sequestering agents, chelating agents, steroids, anti-coagulants, drugs, and combinations thereof.

In one specific embodiment, the continuous phase of the fluorocarbon emulsion can further include a hydrogel. For example, the perfluorocarbon emulsion can be mixed in with a pre-gel solution, optionally along with cells. Cells could also be seeded later, e.g. by perfusion or by migration from the surface. The hydrogel in the bioreactor may include microfabricated channels for perfusion. Incorporating perfluorocarbons in the liquid mobile phase (media supply) would deliver oxygen, while perfluorocarbons in the gel would retain oxygen for longer periods of time. Static cultures of encapsulated or surface-cultured cells may also utilize perfluorocarbons in the media or matrix environment. The encapsulation of perfluorocarbon droplets of the emulsion with a hydrogel can further enhance emulsion stability and reduce or prevent settling of disperse phase droplets. Non-limiting examples of suitable hydrogels include a hyaluronic acid hydrogel and those based on materials such as collagen, silk, acrylates, alginate, fibrin, fibronectin, chitosan, chondroitin sulfate, other glycosaminoglycan or proteoglycans, gelatin, protein, poly-NIPAam, other synthetic polymers and the like, and combinations thereof.

The perfluorocarbon emulsions exhibit substantial stability which broaden potential applications and also usefulness of such artificial oxygen carriers. Most often, the perfluorocarbon emulsions can have an ex vivo stability of a droplet diameter change over three months of less than 50%, often less than 10%, and in many cases less than about 7% at 37° C. Depending on the specific formulation, the droplet diameter change can be statistically insignificant over three months. Furthermore, these perfluorocarbon emulsions can exhibit an in vivo stability wherein the droplets are substantially preserved up to one month in tissue and one week in blood.

The perfluorocarbon emulsions can be used in a number of applications such as, but not limited to, tissue culturing, blood substitutes, liquid breathing, and the like. When preparing the emulsions as a blood substitute antigenicity, reduced or eliminated infection transmission, useful half-life and room temperature stability are all important factors to achieve. The perfluorocarbon emulsions can be used directly as a blood substitute or may further include optional additives such as colloid-osmotic (oncotic) pressure control agents, viscosity control agents, drugs, antibiotics, steroids, or the like. As such, the perfluorocarbon emulsions can be administered to a host for in vivo delivery of oxygen.

A method of delivering oxygen to biological tissue can include exposing the biological tissue to the perfluorocarbon emulsion such as by mixture with a perfusion bioreactor medium, injection, encapsulating cells in gels containing the perfluorocarbon emulsion, culture media, gel, matrix materials, and the like. Such systems can, for example, include perfused or static culture systems. The biological tissue can be a tissue construct, a two-dimensional cell culture, or the like. For example, the perfluorocarbon emulsions can be incorporated into aqueous and/or hydrogel phases of perfusion bioreactors or other culture systems to provide supplemental oxygen to target cells. Further, the emulsion can be formulated specifically for preparation of a blood substitute.

Although other approaches can be useful, the perfluorocarbon emulsions can be made using techniques such as sonication, agitation, mixing, etc. In particular, a perfluorocarbon emulsion can be formed by forming a solution of the polyethylene block copolymer such as by mixing the copolymer into an aqueous solution. The copolymer can be dissolved using a solvent such as 10% dioxane, tetrahydrofuran (THF) or other suitable solvent. This solution can be subjected to dialysis against an aqueous solution (e.g. PBS or other buffered aqueous preparation). The resulting copolymer solution can then be optionally sterile-filtered. The perfluorocarbon can be introduced and mixed into the copolymer solution. In order to prepare a suitable emulsion, the mixture can be mixed and sonicated to obtain the desired emulsion. Other emulsion forming techniques can also be used such as, but not limited to, high shear agitation, homogenization/atomization, and the like.

EXAMPLES

Example 1

Principles of the above-described invention are now illustrated by the following specific examples. These are not to be construed as limiting of the present invention but rather illustrating application of the present invention with a limited number of specific embodiments.

Stable emulsions were prepared by sonicating a mixture of perfluorocarbon (PFC) and PEO-b-PCL stabilizer (poly(ethylene oxide)-block-poly(ε-caprolactone) copolymer available from Polymer Source Inc.) in phosphate buffered saline (PBS) for ten minutes on ice. The PFC used include perfluoro-15-crown-5-ether (PFCE available from Oakwood Products) and perflubron as indicated in the respective figures. More specifically, PEO-b-PCL micelles were formed by dissolution in 10% dioxane, THF or other solvent and dialysis against the aqueous solution. The solution was then filtered. The respective PFC was added and then the solution sonicated at 20 kHz and 5 A for 5-15 minutes on ice to obtain the perfluorocarbon emulsion.

The perfluorocarbon emulsions were saturated by sparging with pure oxygen. The oxygen-saturated emulsions were then exposed to normoxic conditions at 37° C. The oxygen-carrying properties of the emulsions were investigated by measuring the rate of decline of partial oxygen pressure ($pO_2$) of 1 ml oxygen-saturated solutions exposed to ambient air and by measuring the $pO_2$ of various mixtures of oxygen-saturated and depleted solutions, generating a percent saturation curve. Measurements were performed at 37° C. with a Licox pO2 monitor with oxygen and temperature catheter micro-probes and reported in FIG. 1. Significance of the data in comparison with a PBS control was established by two-tailed T-tests. Stability of emulsions stored at 4° C. and 37° C. for 4 weeks was measured by dynamic light scattering measurements of droplet size.

Figure 2A:
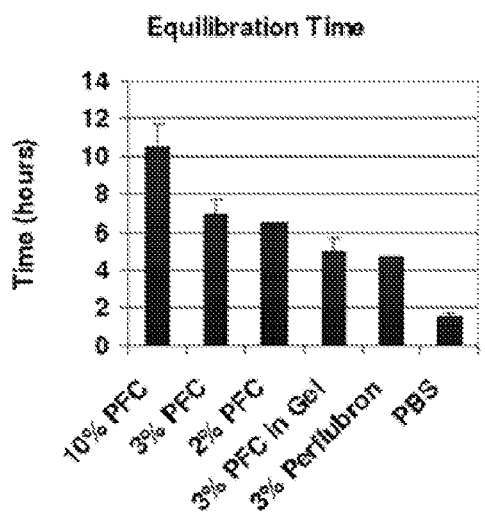
FIGS. 2A and 2B are graphs showing equilibration time and rate of $pO_2$ decline in $O_2$-saturated solutions equilibrating with ambient $pO_2$.
Figure 2B:
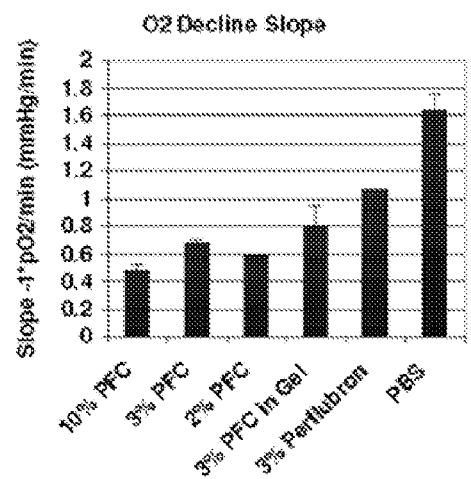

For 10%, 2%, and 3% PFC emulsions, 3% perflubron emulsion, and 3% PFC emulsion in 2% hyaluronic-acid based hydrogel (all examples included PEO-b-PCL). Linear plots ($R^2>0.98$) were generated of $pO_2$ decline of saturated solutions following oxygen sparging. Inverses slopes are compared in FIG. 2 with the lower linear portion of the log-decaying curve of a PBS control. The 10% PFC emulsions exhibited the greatest oxygen affinity, retaining the dissolved gas in solution for over ten hours, as compared to 2 hours for the PBS control. An oxygen saturation curve generated for 2% PFC emulsion showed a linear increase in % saturation or $O_2$ content with increasing $pO_2$.

Figure 3A:
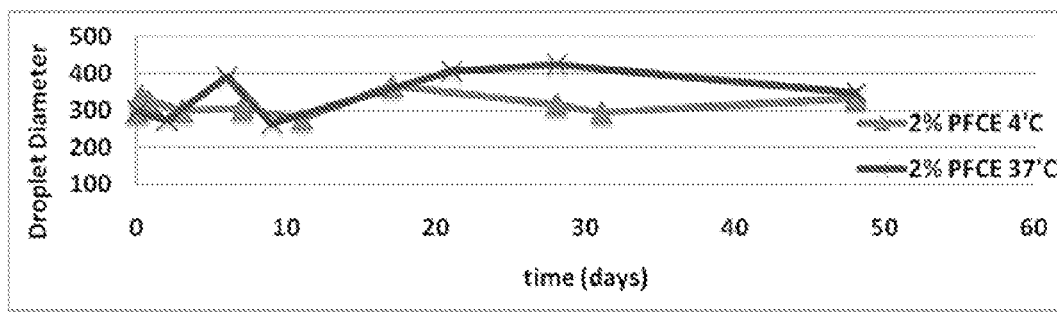
FIG. 3A is a graph of droplet diameter of 2% PFCE emulsions stored at 4° C. and 37° C. over time.
Figure 3B:
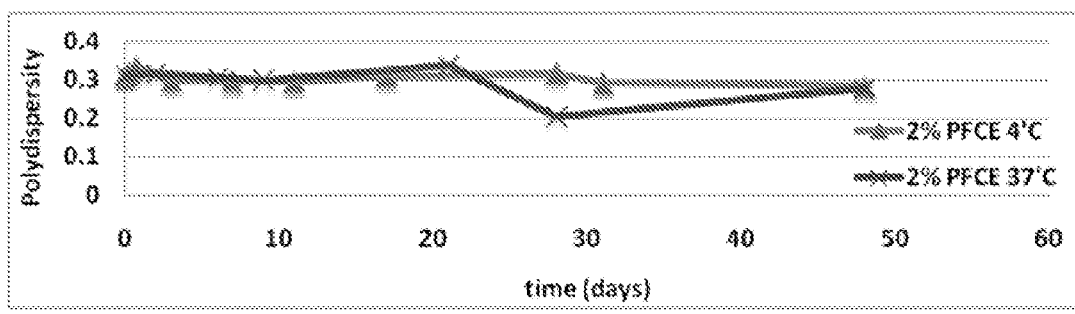
FIG. 3B is a graph of polydispersity index of the same samples as FIG. 3A over time. Cumulative data were obtained from dynamic light scattering analysis. Droplet size was stable over the course of seven weeks. A Delsa™ Nano S particle analyzer was used to collect this data.
Figure 3C:
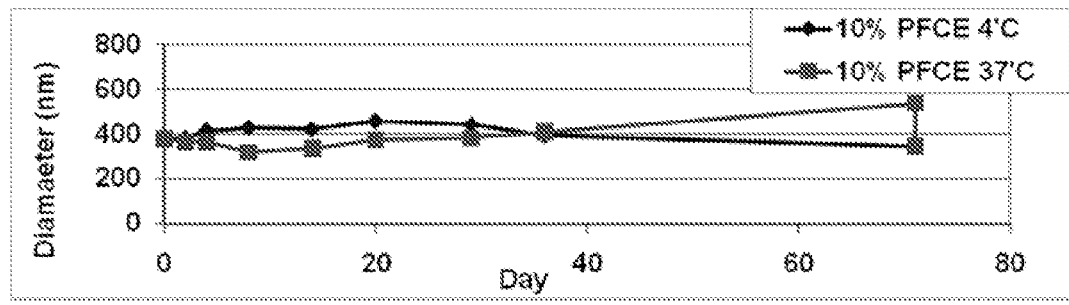
FIG. 3C is a graph of droplet diameter of 10% PFCE emulsions stored at 4° C. and 37° C. over time.
Figure 3D:
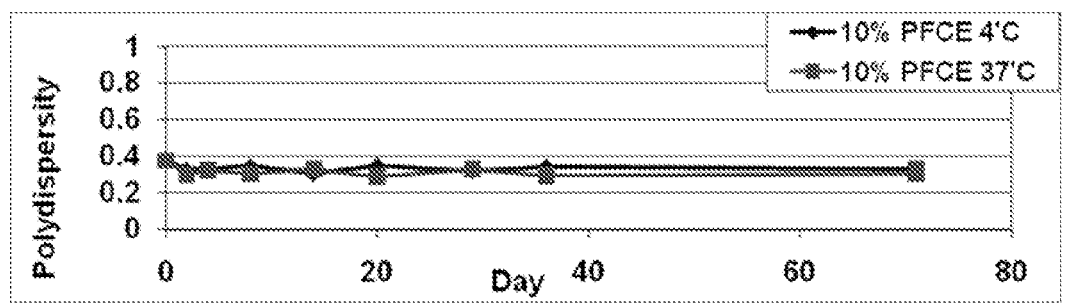
FIG. 3D is a graph of polydispersity index of the same samples as FIG. 3C over time.

As shown in FIG. 3A, light scattering data showed that 2% and 10% PFC emulsions exhibited stable cumulative droplet size of 250-450 nm over four weeks at 37° and 4° C. and even following sonication. As shown in FIG. 3B, the polydispersity index remained below 0.35. Dense (1.7 g/ml) PFC droplets settled after several hours without coalescing and could be resuspended by agitation. These emulsions furthermore exhibited such stability after exposure to sonication and gamma irradiation. FIGS. 3C and 3D show light scattering and polydispersity data for the 10% PFC emulsions at 4° C. and 37° C. for up to 70 days. Furthermore, the 2% PFCE-1.3% PEO-PCL emulsion maintained stable cumulants diameter and polydispersity for 6 months at 4° C.

Under the conditions tested, 2%, 3% and 10% PFC emulsions (including 3% PFC in gel) exhibited greater oxygen affinity than PBS control or 3% perflubron. Furthermore, these emulsions have good oxygen affinity (exceeding perflubron), reaching equilibration in 6-11 hours. Lacking the cooperative $O_2$ binding of hemoglobin, PFCs can stabilize very high oxygen contents and release up to 100% of their load at hypoxic tissues. Good oxygen affinity and stability make these novel AOCs excellent candidates for use in liquid and/or gel phases of perfusion bioreactors, especially if combined with microfluidic channels. Such approaches may enable much tighter control over environmental oxygen tension and a variety of studies of cell behavior in hypoxic and hyperoxic conditions.

Example 2

The same procedures were followed as in Example 1, except a low surfactant to PFC ratio was prepared as follows. This lower ratio is intended to minimize free/micelle surfactant interactions with cell membrane. Low concentration PEO-PCL/PFCE emulsions also demonstrated excellent biocompatibility in mice for chemotherapeutic and imaging applications. A first emulsion of 33% perfluoro-15-Crown-5-Ether (PFCE) (Polymer Source, Montreal, Canada) was prepared with 2% poly(ethylene oxide-b-caprolactone) (PEO- PCL) surfactant (Oakwood Chemical, West Columbia, S.C.). A second emulsion was prepared by dilution to 5% PFCE and 0.3% PEO-PCL.

Example 3

The same procedures were followed as in Example 1, except the stabilizer used was PEO-PLLA (i.e. 5% poly(ethylene oxide-b-L-lactide) in 1% PFCE. The molecular weight of PEO-PCL was 5000-b-4700 and the stabilizer was obtained from (Polymer Source, Montreal, Canada). As with PEO-PCL/PFCE, biocompatibility results from in vivo studies were excellent.

Example 4

The same procedures were followed as in Example 1, except the stabilizer was PEO-PLA (i.e. 3% poly(ethylene oxide-b-lactide from Polymer Source, Montreal, Canada.

Table I shows volume distribution for Examples 1-4.

TABLE I

| Volume Distribution Particle Diameters | | | | | | | | | | |
| --- | --- | --- | --- | --- | --- | --- | --- | --- | --- | --- |
| Surfactant | % | % PFCE | Peak 1 | % | Std Dev | Peak 2 | % | Std Dev | Cum | PDI |
| PEO-PLLA | 0 | 0 | 223 | 1 | 53 | | | | 269 | 0.125 |
| PEO-PLLA | 0 | 0.05 | 331 | 0.75 | 81 | 1848 | 0.2 | 393 | 410 | 0.286 |
| PEO-PLA | 0 | 0 | 343 | 0.15 | 21 | 810 | 0.4 | 112 | 1073 | 0.427 |
| PEO-PCL | 0 | 0.33 | 528 | 0.71 | 128 | 128 | 0.3 | 31 | 363 | 0.337 |

Figure 4:
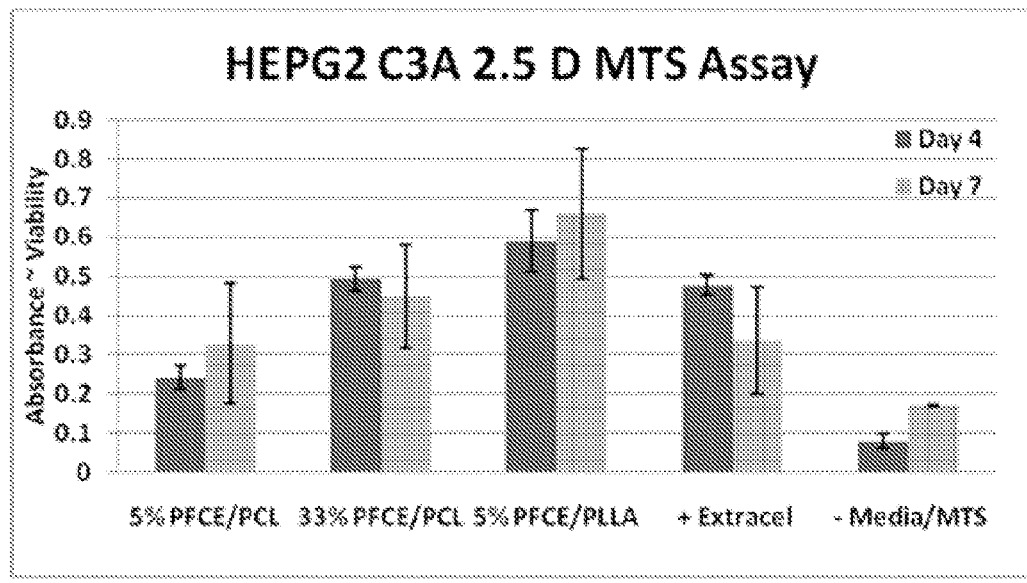
FIG. 4 is a graph of the tetrazolium compound 3-(4,5-dimethylthiazol-2-yl)-5-(3-carboxymethoxyphenyl)-2-(4-sulfophenyl)-2H-tetrazolium, inner salt (MTS) colorometric assay of HEPG2-C3A cells cultured atop 5% emulsion encapsulated within Extracel, a thiol-modified hyaluronan and gelatin hydrogel to show cytocompatibility of PEO-PLLA/PFCE emulsions. The '+' indicates positive control while '−' indicates negative control.
Figure 5:
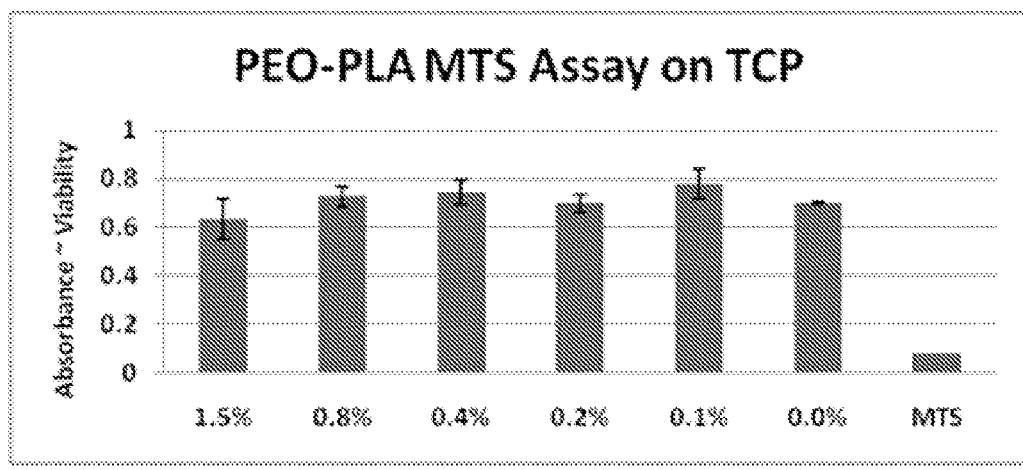
FIG. 5 is a graph of MTS colorometric assay of PEO-PLA on TCP (tissue cultured plastic) of varying concentrations to show cytocompatibility of PEO-PLLA/PFCE emulsions.

Cytocompatibility of PEO-PLLA/PFCE emulsions was established by MTS colorometric assay of HEPG2-C3A cells cultured atop 5% emulsion encapsulated within Extracel, a thiol-modified hyaluronan and gelatin hydrogel (Glycosan Biosciences, Salt Lake City, Utah) as shown in FIGS. 4 and 5. Test metabolic activity exceeded that of both positive and negative controls (Extracel and MTS) on both days 4 and 7. Limited cytocompatibility was also demonstrated for standard and high concentrations of PEO-PCL/PFCE emulsions.

Cytocompatibility of PEO-PLA micelles was demonstrated by culturing NIH CT3 cells for five days in 48 well plates with serial dilutions of the surfactant in media. Semi-quantitative MTS colorimetric cell metabolism indicators were comparable to positive and control (0%) and significantly different from negative control (MTS).

Based on these results, one application is in the mobile phase (perfusate) of perfusion bioreactors where the emulsion can be oxygenated shortly before delivering at hypoxic tissue, in a manner similar to hemoglobin circulation in the body. Incorporation of AOCs into hydrogels may also increase oxygen content and possibly extend diffusion distance from channels. As an illustration, 1 ml $O_2$-saturated PFCE solutions equilibrate with ambient $pO_2$ in over 10 hours, but the oxygen decline rate is much higher in hypoxic conditions, about 15 minutes at $pO_2$=0 mm Hg.

The stability advantage of these emulsions is particularly notable in vivo, where they remained for days to weeks, depending on the tissue, as opposed to hours to days. This is apparently due to the synthetic and physicochemical nature of the surfactants which interact significantly less with cell membranes and lipids. A shelf life of up to a couple years may be expected for some emulsion formulations.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A perfluorocarbon emulsion for use as an artificial oxygen carrier, comprising:
   a) a dispersed phase including a perfluorocarbon and an emulsion stabilizer, said emulsion stabilizer including primarily a poly(ethylene oxide) block copolymer; and
   b) a continuous aqueous phase.

2. The perfluorocarbon emulsion of claim 1, wherein the emulsion stabilizer consists essentially of the poly(ethylene oxide) block copolymer.

3. The perfluorocarbon emulsion of claim 1, wherein the poly(ethylene oxide) block copolymer is biodegradable.

4. The perfluorocarbon emulsion of claim 1, wherein the poly(ethylene oxide) block copolymer is a poly(ethylene oxide)-polyester block copolymer.

5. The perfluorocarbon emulsion of claim 4, wherein the poly(ethylene oxide) block copolymer is selected from the group consisting of poly(ethylene oxide)-block-poly(ε-caprolactone) copolymer, poly(ethylene oxide)-block-(L) polylactide copolymer, poly(ethylene oxide)-block-(D) polylactide copolymer, poly(ethylene oxide)-block-(D,L) polylactide copolymer, and combinations thereof.

6. The perfluorocarbon emulsion of claim 1, wherein the poly(ethylene oxide) block copolymer is a poly(ethylene oxide)-polyether block copolymer.

7. The perfluorocarbon emulsion of claim 6, wherein the poly(ethylene oxide)-polyether block copolymer is a polyethylene-polyether triblock copolymer.

8. The perfluorocarbon emulsion of claim 1, wherein the perfluorocarbon is selected from the group consisting of perfluoro crown ethers, perfluoroalkanes, perfluoropentane, perfluorooctyl bromide, perfluoro cycloalkanes, and mixtures thereof.

9. The perfluorocarbon emulsion of claim 1, wherein the perfluorocarbon is a perfluoroalkyl ether.

10. The perfluorocarbon emulsion of claim 9, wherein the perfluoroalkyl ether is a crown ether.

11. The perfluorocarbon emulsion of claim 10, wherein the perfluoroalkyl ether is perfluoro-15-crown-5-ether having a structure I

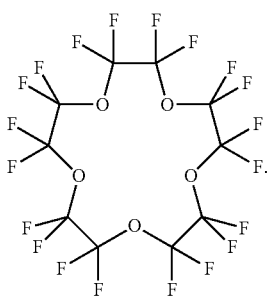 [SMILES: FC1(F)OC(F)(F)C(F)(F)OC(F)(F)C(F)(F)OC(F)(F)C(F)(F)OC(F)(F)C(F)(F)OC1(F)F]

12. The perfluorocarbon emulsion of claim 1, wherein the perfluorocarbon is present from about 1 vol % to about 70 vol % of the perfluorocarbon emulsion.

13. The perfluorocarbon emulsion of claim 1, wherein the perfluorocarbon has a boiling point greater than about 50° C.

14. The perfluorocarbon emulsion of claim 13, wherein the boiling point is greater than about 120° C.

15. The perfluorocarbon emulsion of claim 1, wherein a ratio of stabilizer to perfluorocarbon is about 0.006:1 to about 2:1.

16. The perfluorocarbon emulsion of claim 1, wherein the dispersed phase has a droplet size from about 200 nm to about 500 nm.

17. The perfluorocarbon emulsion of claim 1, wherein the continuous aqueous phase includes a hydrogel.

18. The perfluorocarbon emulsion of claim 17, wherein the hydrogel is a hyaluronic acid hydrogel, collagen, silk, acrylates, alginate, fibrin, fibronectin, chitosan, chondroitin sulfate, gag proteins, proteoglycans, gelatin, protein, poly-NIPAam or combination thereof.

19. The perfluorocarbon emulsion of claim 1, wherein the perfluorocarbon emulsion includes at least one of an anti-oxidant, a sequestering agent, a chelating agent, a steroid, and an anti-coagulant.

20. The perfluorocarbon emulsion of claim 1, wherein the perfluorocarbon emulsion has an ex vivo stability of less than 10% in droplet diameter change over three months.

21. The perfluorocarbon emulsion of claim 1, wherein the perfluorocarbon emulsion exhibits an in vivo stability wherein the droplets are substantially preserved up to one month in tissue and one week in blood.

22. The perfluorocarbon emulsion of claim 1, wherein the perfluorocarbon emulsion is formulated as a blood substitute.

23. The perfluorocarbon emulsion of claim 1, wherein the dispersed phase comprises droplets capable of changing in diameter by less than 50% over three months at 37° C.

24. The perfluorocarbon emulsion of claim 1, wherein the dispersed phase comprises droplets capable of changing in diameter by less than 10% over three months at 37° C.

25. A method of delivering oxygen to biological tissue, comprising exposing the biological tissue to the perfluorocarbon emulsion of claim 1.

26. The method of claim 25, wherein the biological tissue is a tissue construct.

27. The method of claim 25, wherein the biological tissue is in vivo.

* * * * *

UNITED STATES PATENT AND TRADEMARK OFFICE
CERTIFICATE OF CORRECTION

| | | |
|---|---|---|
| PATENT NO. | : 8,673,984 B2 | Page 1 of 1 |
| APPLICATION NO. | : 13/133126 | |
| DATED | : March 18, 2014 | |
| INVENTOR(S) | : Rapoport et al. | |

It is certified that error appears in the above-identified patent and that said Letters Patent is hereby corrected as shown below:

In the specification

Column 1, lines 16-20, delete: "This invention was made with governement support under Grant No. R01 EB1033 awarded by the National Institutes of Health and Graduate Research Fellowship No. 2007051771 awarded by the National Science Foundation. The United States government has certain rights in this invention."

Column 1, line 16, insert: --This invention was made with government support under EB001033 awarded by the National Institutes of Health. The government has certain rights in the invention.--

Signed and Sealed this
First Day of March, 2016

Michelle K. Lee
*Director of the United States Patent and Trademark Office*